U.S. Patent    Jan. 31, 1978    4,071,027
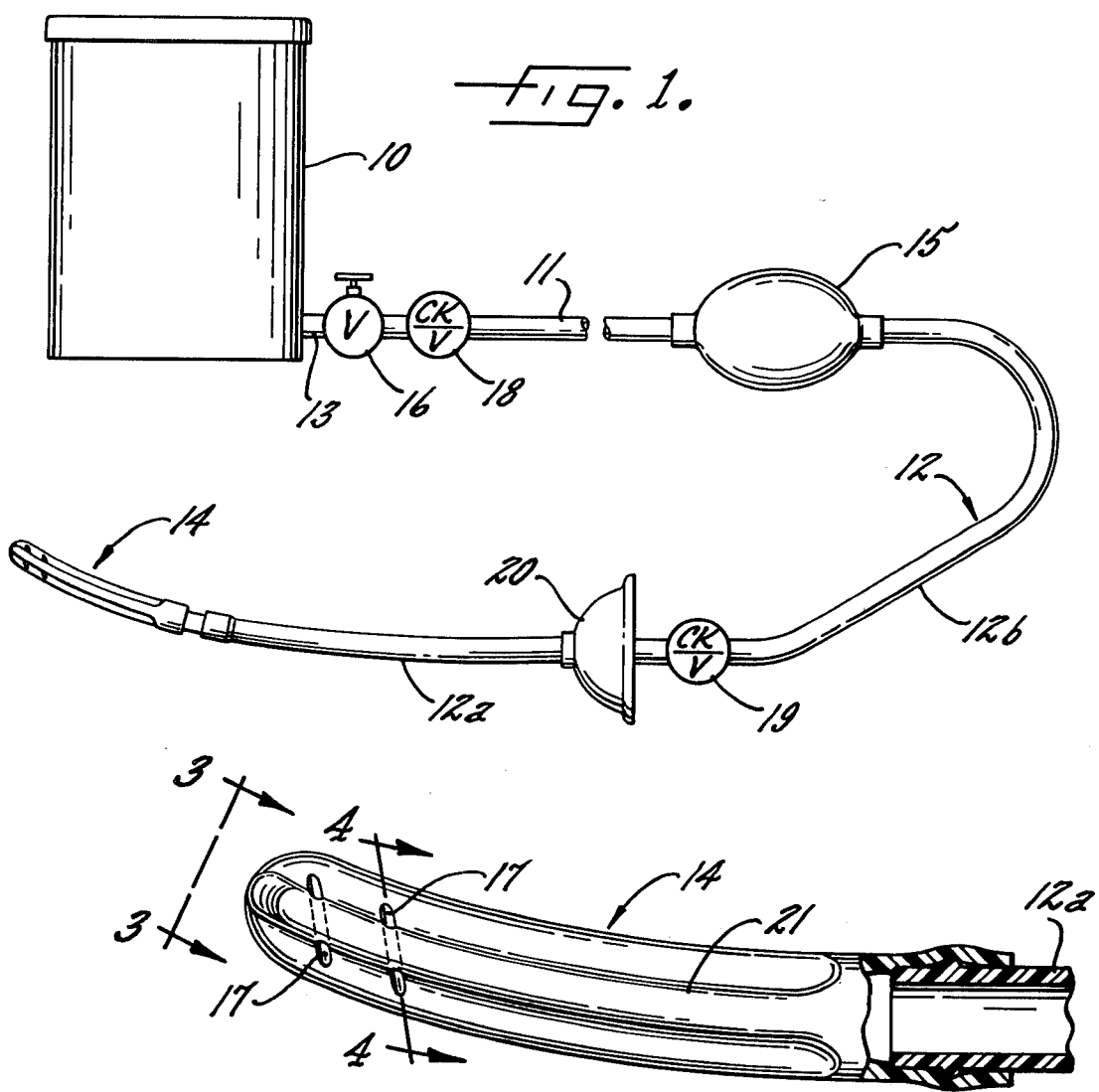
Fig. 1.
Fig. 2.
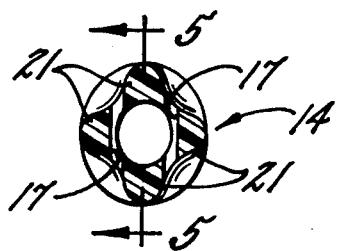
Fig. 3.
Fig. 4.
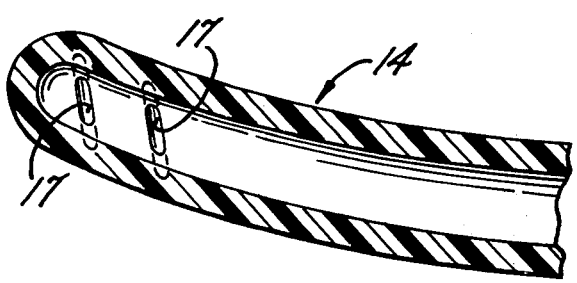
Fig. 5.

United States Patent [19]

Meador

[11] 4,071,027

[45] Jan. 31, 1978

[54] METHOD FOR FLUSHING THE UTERUS OF A SOW

[76] Inventor: Lawrence Dean Meador, R.R. 2, Lanark, Ill. 61046

[21] Appl. No.: 733,159

[22] Filed: Oct. 18, 1976

Related U.S. Application Data

[63] Continuation-in-part of Ser. No. 599,877, Aug. 27, 1975, abandoned.

[51] Int. Cl.² ............................................. A61M 1/00
[52] U.S. Cl. .................................................. 128/231
[58] Field of Search ............... 128/231, 227, 239, 245, 128/232, 251, 248, 222, 223

[56] References Cited

U.S. PATENT DOCUMENTS

| | | | |
|---|---|---|---|
| 906,711 | 12/1908 | Hill et al. | 128/231 |
| 926,197 | 6/1909 | Kim | 128/231 |
| 969,482 | 9/1910 | Jones | 128/231 |
| 1,076,425 | 10/1913 | Holland | 128/239 |
| 1,098,220 | 5/1914 | Borsody | 128/239 |
| 1,493,592 | 5/1924 | Beck | 128/231 |
| 1,494,985 | 5/1924 | Beck | 128/231 |
| 1,497,264 | 6/1924 | Gurnee et al. | 128/239 |
| 2,023,026 | 12/1935 | Miller | 128/227 |
| 2,768,624 | 10/1956 | Lamb | 128/227 |
| 3,422,814 | 1/1969 | Lloyd | 128/245 |
| 3,474,788 | 10/1969 | Corbin et al. | 128/239 X |

*Primary Examiner*—John D. Yasko
*Attorney, Agent, or Firm*—Leydig, Voit, Osann, Mayer & Holt, Ltd.

[57] ABSTRACT

Method and apparatus for flushing the uterus of a sow wherein the apparatus includes a reservoir for holding a supply of uterine flushing liquid and a first flexible hose is connected to the outlet of the reservoir with a check valve near the outlet to prevent liquid from flowing back into the reservoir. A squeeze bulb is interposed between the end of the hose and a second hose which also contains a check valve intermediate its ends to prevent liquid from flowing back toward the bulb. A relatively rigid but soft tip is connected to the outer end of the second hose at an angle thereto for insertion selectively into the uterine horns of a sow. When the bulb is squeezed, liquid flows out of holes in the tip adjacent the end thereof and into the horn.

2 Claims, 5 Drawing Figures

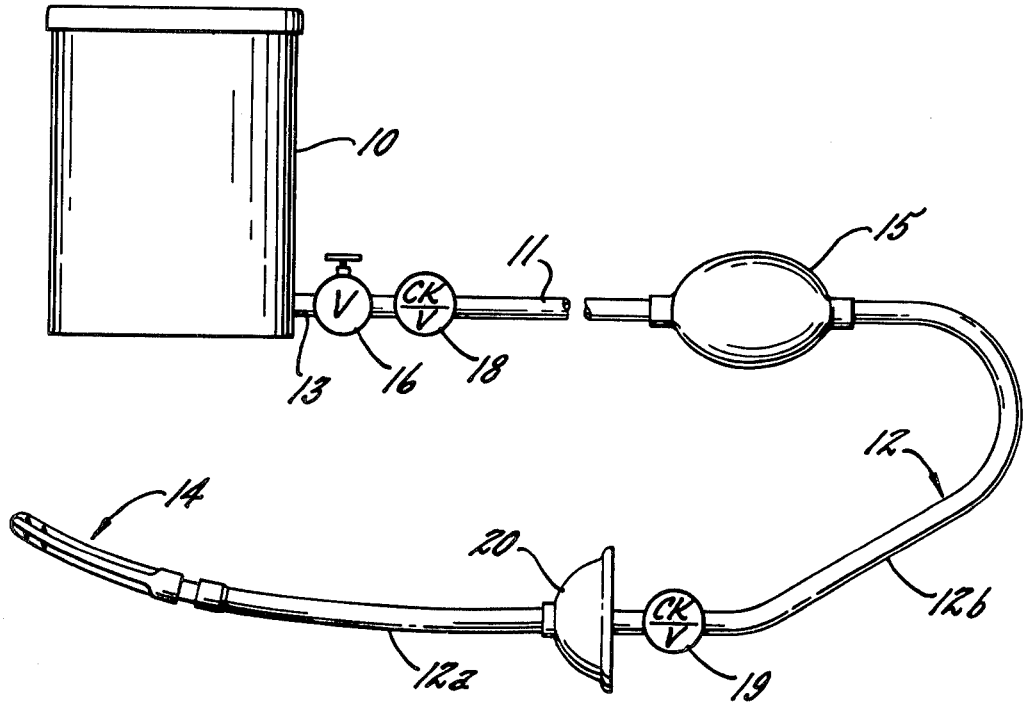

METHOD FOR FLUSHING THE UTERUS OF A SOW

CROSS-REFERENCE TO RELATED APPLICATION

This application is a continuation-in-part of my co-pending application Ser. No. 599,877, filed Aug. 27, 1975 now abandoned.

BACKGROUND OF THE INVENTION

In farrowing, the uterus and particularly the uterine horns of the sow may be injured and subject to infection. If infection occurs, this may affect the mammary glands of the sow and possibly infect the suckling pigs.

SUMMARY OF THE INVENTION

The general object of the present invention is to provide a novel apparatus and method for flushing the uterine horns of a sow shortly after farrowing to reduce the possibility of the horns becoming infected.

A more detailed object is to provide an apparatus which holds a supply of medicated flushing liquid and which delivers the liquid to the sow's uterine horns through hoses and a tip which is arranged in a novel manner so that it is comparatively easy to insert in each horn.

Another object is to combine the hoses with check valves and a squeeze bulb to utilize the hoses as a means to meter the liquid delivered to a horn.

The invention also resides in the method of using the novel apparatus.

BRIEF DESCRIPTION OF THE DRAWINGS

FIG. 1 is a general view of the apparatus showing my invention, portions being shown schematically.

FIG. 2 is an enlarged fragmentary view of the tip, portions being broken away and shown in section.

FIG. 3 is an end view of the tip as seen along the line 3—3 in FIG. 2.

FIG. 4 is a sectional view taken along the line 4—4 in FIG. 2.

FIG. 5 is a fragmentary sectional view taken along the line 5—5 in FIG. 4.

DETAILED DESCRIPTION OF THE PREFERRED EMBODIMENT

When a sow farrows, the pigs to be born are squeezed out of the horns of the sow's uterus and this can cause the uterine horns to be scratched. As a result, the horns may become infected and such infection may affect the mammary glands of the sow and hence the health of the suckling pigs.

The present invention contemplates the provision of a novel method and apparatus for flushing the horns of a sow with a medicated liquid to substantially reduce the possibility of infection of the sow's uterus. In general, the apparatus includes a reservoir 10 for holding a supply of medicated liquid, hosing or tubing 11, 12 extending from the outlet 13 of the reservoir, a tip 14 secured to the free end of the tubing and extending at an angle thereto, and means including a squeeze bulb pump 15 interposed in the tubing and operable when squeezed and when the tip is inserted into a uterine horn of a sow to inject a metered amount of liquid into the horn.

In the present instance, the reservoir 10 is an acid-resistant plastic tank capable of holding several gallons of medicated liquid and the outlet 13 is a pipe fitting communicating with the inside of the tank against the bottom thereof. A conventional shut-off valve 16 is connected to the fitting 13 and one end of a section 11 of hose or tubing is attached to the valve, the hose section 11 being of any suitable length convenient for use. The other end of the hose section 11 is connected to one side of the pump 15 of the squeeze ball variety and one end of a second hose or tube section 12 of a preselected length for metering purposes is connected to the other side of the squeeze ball 15. The tip 14 is closed at the outer end and has a plurality of holes 17 adjacent the closed end, the tip being telescoped snugly over the free end of the hose section 12 as seen most clearly in FIG. 2. The hose section 12 may be formed in two pieces $12^a$ and $12^b$ with at least the section $12^a$ being made of a relatively rigid plastic so as to enter the cervix of a sow as will be explained later more in detail. The hose sections 11 and $12^b$ are made of a plastic material which is quite flexible even when cold and can withstand medicines such as iodine and the tip 14 is molded from a material which is fairly soft but is relatively rigid as compared to the hose sections. A suitable material for the hose sections 11 and $12^b$ is a high grade polyvinyl chloride with plasticizers but without extenders of fillers and, for the hose section $12^a$, a plastic sold and identified by Goodall Rubber Company of Trenton, N.J. as CSM Hypalon. Surgical rubber may be used for the tip 14.

A check valve 18 is interposed in the hose section 11 near the shut-off valve and is arranged to allow liquid to flow out of the tank 10 and into the hose sections 11 and 12 and the bulb 15 but prevents the liquid from flowing back into the tank when the bulb is squeezed. A second check valve 19 is interposed in the hose section 12 intermediate the ends thereof and this check valve is arranged to permit liquid to flow through the hose section 12 and the tip 14 and out through the holes 17 when the bulb 15 is squeezed but prevents the liquid from backing up from the tip when the bulb is released. A round shield 20 made of a soft plastic material and flaring rearwardly away from the tip 14 is mounted on the hose section 12 in front of the check valve 19 and, as will be described more in detail later, limits the amount of hose that can be inserted in the uterus of the sow.

One important aspect of the invention is the construction of the tip 14 and its relationship to the hose section $12^a$. Thus, the tip is disposed at an angle to the free end portion of the section $12^a$ and this permits the gentle entry of the tip from the uterine canal into a uterine horn. Preferably, the tip is slightly curved and the average angle of the tip relative to the section $12^a$ is between 10° and 15°. Herein, the tip is shaped to have four longitudinal ribs 21 equally spaced around the tip and gently rounded along their outer sides (see FIGS. 4 and 5). Two holes 11 project through each valley between adjacent ribs 21 and are inclined forwardly to obtain better circulation of the liquid into the folds of the horns. In the preferred form, the holes are tilted about 30 degrees forward from the perpendicular.

In use, a medicated liquid preferably as prescribed by a veterinarian is poured into the reservoir 10. The valve 16 then is opened and the tubing or hose sections 11 and 12, the bulb 15 and the tip 14 are filled with the liquid either by gravity or by squeezing the bulb or both. Next, the tip and the hose section $12^a$ are inserted into the uterine canal of the sow with the tip pointed down toward the sow's underline. As the tip enters through the hip bones, the tubing $12^a$ and hence the tip are turned 90° either right or left and the insertion is continued. This causes the tip to slip gently through the cervix and into the corresponding horn. The insertion continues until the shield 20 is pressed against the vulva and then the bulb 15 is squeezed a number of times until the desired amount of liquid has been injected into the horn. To flush the other horn, the tip is retracted to about the hip bones and the tubing and tip are turned 180° in the opposite direction. The tip then is pushed in and enters the other horn and the latter is flushed in the same manner as the first horn. Finally, the tip and tubing are removed from the sow and the flushing is complete.

By making the hose section 12 of a preselected length, it can be determined by calculation or simple testing the amount of liquid which is ejected from the tip 14 each time the bulb 15 is squeezed. Thus, when the bulb is squeezed, the check valve 18 closes and the liquid in the hose section 11 does not move. At the same time, the check valve 19 opens and a generally uniform proportion of the liquid in the bulb 15, the hose section 12 and the tip 14 flows out of the tip. It has been found that a convenient arrangement is to size hose section 12 so that one quart of liquid is ejected when the bulb is squeezed four times, this being the amount of liquid usually desirable to flush one horn of a sow.

I claim:

1. The method of flushing the uterine horns of a sow after farrowing with a reservoir containing flushing fluid, flexible tubing communicating with said reservoir, a squeeze bulb interposed in said tubing intermediate the ends thereof and a soft but relatively rigid hollow tip connected to the free end of said tubing at an angle thereto and having holes through which the liquid may flow, said method comprising the steps of, inserting the tip into the uterine canal of a sow with the tip pointed down toward the sow's underline, such insertion continuing until the tip enters through the hip bones of the sow, turning said tip 90° in one direction, thereafter continuing the insertion until the tip enters ones uterine horn of the sow, squeezing said bulb to inject said liquid into said horn, thereafter retracting said tip to a point adjacent said hip bones and turning the tip 180° in the opposite direction, inserting said tip into the other uterine horn of the sow, squeezing said bulb to inject said liquid into said other horn, and retracting the tip and the tubing from the uterus of the sow.

2. The method as defined by claim 1 in which a soft flexible shield encircles said tubing a predetermined distance from said tip and the tip is inserted into each of said uterine horns until said shield presses against the vulva of the sow.

* * * * *